(12) United States Patent
Axelrod et al.

(10) Patent No.: US 8,916,179 B2
(45) Date of Patent: Dec. 23, 2014

(54) ASCOPHYLLUM NODOSUM ANIMAL CHEWS

(75) Inventors: Glen S. Axelrod, Colts Neck, NJ (US); Ajay Gajria, Maharashtra (IN)

(73) Assignee: T.F.H. Publications, Inc., Neptune City, NJ (US)

( * ) Notice: Subject to any disclaimer, the term of this patent is extended or adjusted under 35 U.S.C. 154(b) by 0 days.

(21) Appl. No.: 13/280,862

(22) Filed: Oct. 25, 2011

(65) Prior Publication Data

US 2013/0101648 A1    Apr. 25, 2013

(51) Int. Cl.

| | | |
|---|---|---|
| *A61K 8/97* | (2006.01) | |
| *A61K 8/02* | (2006.01) | |
| *A61Q 11/00* | (2006.01) | |
| *B05D 3/00* | (2006.01) | |
| *B29C 47/06* | (2006.01) | |
| *B29C 47/00* | (2006.01) | |
| *B29B 7/48* | (2006.01) | |
| *B29C 47/38* | (2006.01) | |
| *B29C 47/40* | (2006.01) | |
| *B29C 47/76* | (2006.01) | |

(52) U.S. Cl.
CPC ......... *B29C 47/0021* (2013.01); *B29C 47/0011* (2013.01); *A61Q 11/00* (2013.01); *B29C 47/003* (2013.01); *B29B 7/484* (2013.01); *A61K 8/975* (2013.01); *B29C 47/0038* (2013.01); *B29C 47/767* (2013.01); *B29C 47/0004* (2013.01); *B29C 47/38* (2013.01); *B29C 47/40* (2013.01); *B29C 47/0033* (2013.01)
USPC .............. 424/401; 424/57; 424/58; 427/2.29; 264/129

(58) Field of Classification Search
CPC ........ A61Q 11/00; A61K 8/975; B29B 7/484; B29C 47/0011; B29C 47/0021; B29C 47/003; B29C 47/0033; B29C 47/0038; B29C 47/38; B29C 47/40; B29C 47/0004; B29C 47/767
See application file for complete search history.

(56) References Cited

U.S. PATENT DOCUMENTS 4,581,233 A    4/1986   Herve et al.
4,775,525 A   10/1988   Pera
(Continued)

FOREIGN PATENT DOCUMENTS

JP    56-113269    9/1981
JP    56-117777    9/1981
(Continued)

OTHER PUBLICATIONS

PlaqueOff (California Veterinary Supply http://www.calvetsupply.com/browseproducts/PlaqueOff---Large-180-gm..HTML (2008) pp. 1-3.*

(Continued)

*Primary Examiner* — Kortney L Klinkel
*Assistant Examiner* — Lisbeth C Robinson
(74) *Attorney, Agent, or Firm* — Grossman, Tucker, Perreault & Pfleger, PLLC

(57) ABSTRACT

An animal chew including a surface comprising a base composition, wherein the animal chew exhibits a hardness in the range of Shore 70A to Shore 70D as measured by ASTM D2240-05 (2010) and a flexural modulus in the range of $50\times10^3$ psi to $500\times10^3$ psi as measured by ASTM D790-10 and *Ascophyllum nodosum* applied onto at least a portion of the surface of the animal chew, wherein the *Ascophyllum nodosum* is present in an amount of 0.1% by weight to 5.0% by weight of the animal chew. At least 10% by weight of the total amount of the *Ascophyllum nodosum* present in the animal chew may be applied to the animal chew surface.

6 Claims, 6 Drawing Sheets

(56) References Cited

U.S. PATENT DOCUMENTS

| | | | |
|---|---|---|---|
| 4,857,331 A | 8/1989 | Shaw et al. | |
| 5,310,541 A * | 5/1994 | Montgomery | 424/50 |
| 5,539,133 A | 7/1996 | Kohn et al. | |
| 5,650,412 A | 7/1997 | Kim et al. | |
| 6,013,632 A | 1/2000 | Jones et al. | |
| 6,200,616 B1 | 3/2001 | Axelrod et al. | |
| 6,224,871 B1 | 5/2001 | Hastings et al. | |
| 6,338,856 B1 | 1/2002 | Allen et al. | |
| 6,428,817 B1 | 8/2002 | Collin | |
| 6,495,530 B1 | 12/2002 | Daniels | |
| 7,125,555 B2 | 10/2006 | Wikner | |
| 2004/0022806 A1* | 2/2004 | Wikner | 424/195.17 |
| 2004/0025803 A1 | 2/2004 | Sherrill et al. | |
| 2004/0131732 A1* | 7/2004 | Axelrod et al. | 426/132 |
| 2006/0105025 A1* | 5/2006 | Hill et al. | 424/442 |
| 2007/0031557 A1* | 2/2007 | Axelrod et al. | 426/516 |
| 2007/0098840 A1* | 5/2007 | Axelrod | 426/2 |
| 2008/0185746 A1* | 8/2008 | Axelrod et al. | 264/37.27 |
| 2008/0206405 A1* | 8/2008 | Axelrod et al. | 426/72 |
| 2010/0224138 A1* | 9/2010 | Axelrod et al. | 119/710 |
| 2010/0239487 A1 | 9/2010 | Constantz et al. | |

FOREIGN PATENT DOCUMENTS

| | | |
|---|---|---|
| WO | 89/07437 | 8/1989 |
| WO | 00/13531 | 3/2000 |

OTHER PUBLICATIONS

"Dental Products", "Modern Technology of Cosmetics", National Institute of Industrial Research, Oct. 1, 2004, Cover, front matter and pp. 236-237.*

International Search Report and Written Opinion from corresponding PCT Application No. PCT/US12/59897 dated Jan. 4, 2013.

* cited by examiner

US 8,916,179 B2

ASCOPHYLLUM NODOSUM ANIMAL CHEWS

FIELD OF INVENTION

The present disclosure relates to animal chews including *Ascophyllum nodosum*, a process of forming the animal chews including *Ascophyllum nodosum* and a method of treating animal plaque with the animal chews including *Ascophyllum nodosum*.

BACKGROUND

Animal pets, such as dogs and cats, like their human counterparts, are subject to dental health problems including dental plaque and calculus (i.e., tartar). Dental plaque may include multiple species of bacteria that adhere to the surface of teeth. While dental plaque may initially be soft and easily removed, it may begin to harden within 48 hours and within about 10 days, the plaque may transform into dental calculus, which is relatively hard and difficult to remove. Dental plaque may also lead to tooth decay due to acid produced from the bacterial degradation of fermentable sugars and periodontal problems such as gingivitis and chronic periodontitis. If left untreated, the bacteria may spread to cause malodor, periodontal disease, gingival pockets and bone loss.

To address this problem, a variety of products have been manufactured to provide animal pets with objects to chew or gnaw. These products are intended to provide the pet with exercise for the teeth to maintain a healthy oral condition and satisfy a need that arose when the natural pet food, raw meat, was replaced with processed pet foods. While a number of products have been introduced to mechanically remove plaque from the teeth of animal pets, there still remains room for improvement.

SUMMARY

In one aspect, the present disclosure relates to an animal chew. The animal chew may include a base composition and *Ascophyllum nodosum* applied onto at least a portion of the surface of the animal chew, wherein the *Ascophyllum nodosum* is present in an amount of 0.1% by weight to 5.0% by weight of the animal chew. The animal chew may also exhibit a hardness in the range of Shore 70A to Shore 70D as measured by ASTM D2240-05 (2010) and a flexural modulus in the range of $50 \times 10^3$ psi to $500 \times 10^3$ psi as measured by ASTM D790-10.

In another aspect, the present disclosure relates to a method of forming an animal chew. The method may include plasticating a base composition and forming the base composition into a shape having a surface. The method may also include applying *Ascophyllum nodosum* to at least a portion of the chew surface, wherein the *Ascophyllum nodosum* is added in an amount of 0.1% by weight to 5.0% by weight of the animal chew.

In yet another aspect, the present disclosure relates to a method of treating dental plaque or tartar in an animal's mouth. The method may include providing to an animal an animal chew having a surface including a base composition, wherein the wherein the animal chew exhibits a hardness in the range of Shore 70A to Shore 70D as measured by ASTM D2240-05 (2010) and a flexural modulus in the range of $50 \times 10^3$ psi to $500 \times 10^3$ psi as measured by ASTM D790-10. The animal chew may also include *Ascophyllum nodosum* applied onto at least a portion of the surface of the animal chew, wherein the *Ascophyllum nodosum* is present in an amount of 0.1% by weight to 5.0% by weight of the animal chew and at least 10% by weight of the total amount of said *Ascophyllum nodosum* present in the animal chew is applied to said surface.

BRIEF DESCRIPTION OF THE DRAWINGS

The detailed description below may be better understood with reference to the accompanying figures which are provided for illustrative purposes and are not to be considered as limiting any aspect of the invention.

DETAILED DESCRIPTION

The present disclosure relates to animal chews including *Ascophyllum nodosum* seaweed, or kelp. The present disclosure also relates to a process of forming the animal chews including *Ascophyllum nodosum* and a method of treating animal plaque with the animal chews including *Ascophyllum nodosum*. In some embodiments, the animal chew may be formed out of a base composition on which the *Ascophyllum nodosum* may be incorporated. In further embodiments, the *Ascophyllum nodosum* may also optionally be included within the base composition. The base composition may include biocompatible resins, including synthetic or edible natural or naturally derived resin, and molded using a number of molding processes. In other embodiments, the base composition may be formed out of rawhide. The animal chews including the *Ascophyllum nodosum* may be used to treat animal plaque and calculus through the removal of plaque through mechanical abrasion and/or biological action.

Figure 1:
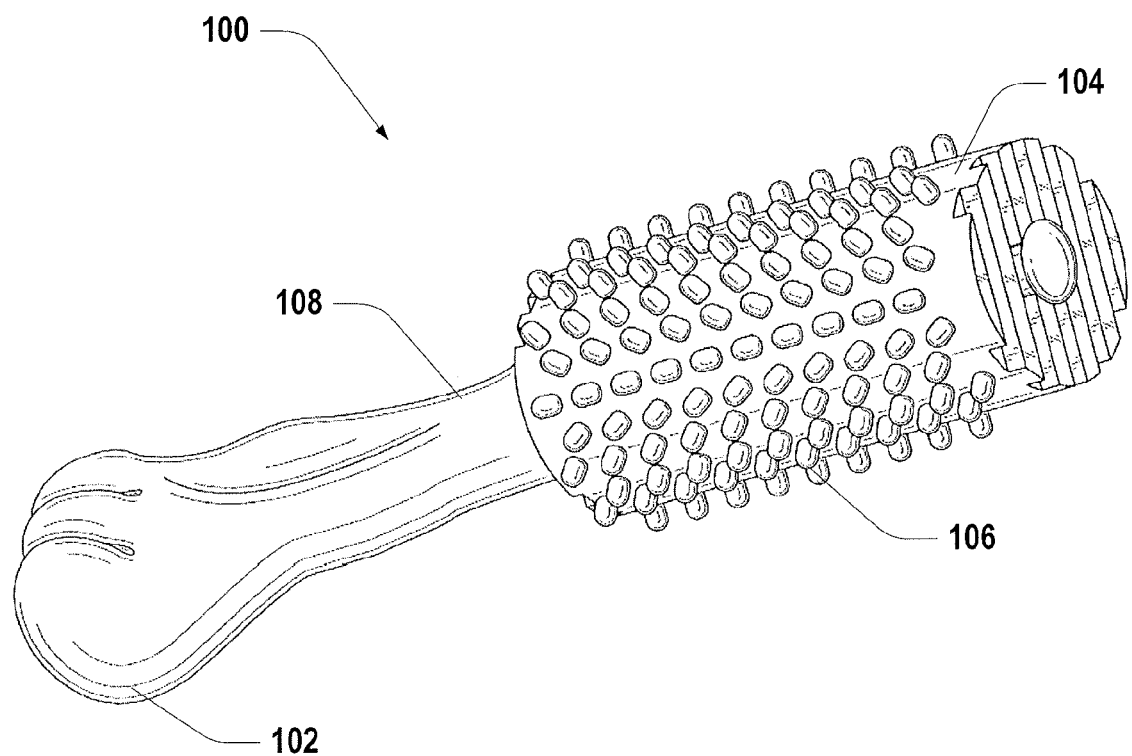
FIG. 1 illustrates a perspective view of an embodiment of an animal chew that may incorporate *Ascophyllum nodosum;*

An example of a non-limiting embodiment of an animal chew contemplated herein is illustrated in FIG. 1. The animal chew 100 may take on a number of forms, in the illustration, the animal chew 100 includes a bulbous end portion 102 and a cylindrical portion 104 including a number of projections 106 therefrom. Other forms may also be provided, such as bone shapes, geometric shapes or shapes simulating various food products, such as a fish, a shish-ka-bob, bacon or a rack of ribs.

As alluded to above, the animal chew may include a biocompatible resin, which may include synthetic or natural or naturally derived resins. Biocompatible resins may include resins that do not exhibit toxic and/or injurious effects on biological systems, such as the digestive track of an animal. Such biocompatible resins may be edible but may or may not be digestible. Non-limiting examples of synthetic resin may include polyurethane, nylon, rubber, etc. A non-limiting example of edible natural or naturally derived resins may include starch or starch based resins. In further embodiments, the animal chew may include rawhide.

The resulting animal chew may exhibit a sufficient hardness and ductility to be repeatedly mechanically abraded by an animal's teeth before the structural integrity of the chew is reduced and breaks into one or more pieces. This in turn can provide an initial effect on the oral cavity. In a preferred embodiment, the hardness of the molded animal chews, as measured by ASTM D2240-05 (2010), may be in the range of Shore 70A to Shore 80D, including all values and whole number ranges therein, including e.g. 98A, 50D, etc. In particularly preferred embodiment, the hardness of the formed animal chew may be in the range of 25 to 40 Shore D, including 30 to 33 Shore D. The animal chew may also exhibit an elongation at break, as measured by ASTM D638-10, in the range of 0.5% to 600% and all values therein in 1% increments, such as 1% to 7%. In addition, the tensile modulus of the animal chew, as measured by ASTM D638-10, may be in the range of $50 \times 10^3$ psi to $500 \times 10^3$ psi, including all values and ranges therein, such as $50 \times 10^3$ psi to $300 \times 10^3$ psi, in 1 psi increments. Furthermore, the flexural modulus of the animal chew may be in the range of $50 \times 10^3$ psi to $500 \times 10^3$ psi, as measured by ASTM D790-10, including all values and ranges therein, such as $50 \times 10^3$ psi to $300 \times 10^3$ psi, in 1 psi increments. An individual animal chew may exhibit one or more of the above properties, i.e., hardness, elongation at break, and tensile modulus.

It has been found that dogs of various breeds may exhibit bite forces in the range of 3 pounds force to 313 pounds force depending on the dog. Accordingly, it may be appreciated that with respect to domestic animals, such hardness values and elongation characteristics will, as noted, now allow the animal chew to be mechanically abraded by the animal's teeth before the chew structural integrity is reduced and it naturally separates into a plurality of pieces for ingestion. In some embodiments, for example, the animal chews may exhibit a sufficient hardness and ductility to be repeatedly mechanically abraded by the teeth of an animal for at least 30 seconds before the structural integrity of the chew is reduced such that the animal chew breaks into one or more pieces. In some embodiments, mechanical abrasion may occur in the range of 5 minutes to 12 hours before the animal chew breaks into one or more pieces, including all values and ranges therein, such as 5 to 10 minutes, 1 hour to 6 hours, etc. Scarring or marring of the surface of the animal chew may occur with mechanical abrasion, although the structural integrity of the chew may remain preserved. The above recited properties therefore ensure *Ascophyllum nodusum* will reside directly in the oral cavity such that it may be combined with saliva from the gums and provide an initial beneficial and timely effect on plaque and/or dental calculus. While the ensuing consumption of the *Ascophyllum nodusum* may then occur, the ability to now ensure a regulated delivery in the oral cavity, for a controlled period of time, is herein contemplated to boost the overall ability to reduce bacterial plaque and dental caries of the animal.

The aforementioned starch compositions may include any carbohydrate of natural or vegetable origin. The starch may include amylose and/or amylopectin and may be extracted from plants, including but not limited to potatoes, rice, tapioca, corn and cereals such as rye, wheat, and oats. The starch may also be extracted from fruits, nuts and rhizomes, or arrowroot, guar gum, locust bean, arracacha, buckwheat, banana, barley, cassava, konjac, kudzu, oca, sago, sorghum, sweet potato, taro, yams, fava beans, lentils and peas. The starch may be present between about 30-99% including all increments and values therebetween such as levels above about 50%, 85%, etc.

The starch employed herein may be raw starch, which may be understood as starch that has not seen a prior thermal molding history, such as extrusion or other type of melt processing step. The raw starch itself may also be native, which may be understood as unmodified starch recovered in the original form by extraction and not physically or chemically modified. The raw starch may also be in powder form of varying particle size, which may be understood as milled and/or pre-sifted. It should be understood that the raw starch may also have varying degrees moisture present.

*Ascophyllum nodosum* seaweed may be added to the animal chew before, during or after forming of the resin or rawhide into an animal chew. The *Ascophyllum nodosum* seaweed may contribute to the mechanical removal of dental plaque or tartar, biological removal of dental plaque or tarter, or both. *Ascophyllum nodosum* seaweed may be understood to be a large, common brown alga of the class Phaeophyceae. It may be found in the northern Atlantic Ocean and, particularly, the north-western coast of Europe, east Greenland and the north-eastern coast of North America. It may be commonly referred to as rockweed, Norwegian kelp, knotted kelp, knotted wrack, or egg wrack. *Ascophyllum nodosum* may be understood to include marcronutrients such as N, P, K, Ca, Mg, S and micronutrients such as Mn, Cu, Fe, Zn, etc. Furthermore, it may include cytokinins, auxin-like substances, gibberellins, betaines, mannitol, organic acids, polysaccharides, amino acids and proteins.

In some embodiments, at least 10% by weight, including all values and ranges from 10% to 100% by weight, of the total amount of the *Ascophyllum nodosum* present in the animal chew may be applied to the surface of the base composition after processing, as illustrated further herein. In further embodiments, the *Ascophyllum nodosum* may also be added and mixed into the base composition before or during processing.

The *Ascophyllum nodosum* may be added to the base composition in the form of a powder and/or an extract. The powder may have an average diameter in the range of 0.01 mm to 1.0 mm, including all values and ranges therein. In other embodiments, the *Ascophyllum nodosum* may be provided as flakes having an average size (longest linear dimension) in the range of 0.1 mm to 5.0 mm, including all values and ranges therein. In yet further embodiments, the *Ascophyllum nodosum* may be dehydrated increasing the hardness of the seaweed to provide an initial effect through mechanical action in the mouth of the animal upon chewing. In yet additional embodiments, the *Ascophyllum nodosum* may be formed into sheets and wrapped around the animal chew or provided in alternating layers the *Ascophyllum nodosum* and the base composition.

In some embodiments, the *Ascophyllum nodosum* may be added in an amount of 0.1% by weight to 5.0% by weight of the total composition of the animal chew, including all values and ranges therein, such as in the range of 0.5% by weight to 2.0% by weight, etc. The total composition of the animal chew may be understood as the amount of base resin as well as any other additives. In other embodiments, the

*Ascophyllum nodosum* may be added to the animal chew in an amount of 0.1 grams to 6 grams, including all values and ranges therein. The amount of the *Ascophyllum nodosum* may be adjusted depending on factors such as the size of the dog. Table 1 illustrates examples of various loadings for various dog sizes.

TABLE 1

Ascophyllum nodosum additions.

| Animal Treat Weight (grams) | Amount of Additive (grams) | Percentage Load in Treat (%) | Size of Animal |
|---|---|---|---|
| 5 | 0.1 | 2.0 | up to 15 lbs. |
| 14 | 0.2 | 1.4 | up to 25 lbs. |
| 27 | 0.3 | 1.1 | up to 35 lbs. |
| 52 | 0.4 | 0.8 | up to 50 lbs. |
| 115 | 0.6 | 0.5 | over 50 lbs. |

In other embodiments, the *Ascophyllum nodosum* seaweed, when in "dry" form (e.g., powder, flake, sheet, etc.) may be added in amount of at least 10 mg per 1 cubic inch of an animal chew including all values and ranges from 10 mg to 2000 mg per 1 cubic inch of an animal chew. In some embodiments, the *Ascophyllum nodosum* may be added in amount of 10 mg to 200 mg per 1 cubic inch of an animal chew including edible resin, including all values and ranges therein, which may be adjusted depending on the size animal. For synthetic resins, the *Ascophyllum nodosum* may be added in amount of 10 mg to 200 mg per 0.5 cubic inches of an animal chew including edible resin, including all values and ranges therein, which may be adjusted based on the size of the animal and the aggressiveness of the animal's chewing. In the case of extracts, the extracts may be added in amounts of comparable efficacy to the above recited dosages for dry seaweed regardless of form (powder, flake, etc.).

Referring again to FIG. 1, the *Ascophyllum nodosum* may be provided on the suface 108 of the animal chew 100 and in some examples the *Ascophyllum nodosum* may be provided through the volume of the animal chew. Furthermore, the *Ascophyllum nodosum* may be provided at selected locations, such as on raised projections 106 or at end portions 102 of the animal chew, again either within the volume of the selected locations or on the surface of such locations.

The base composition may also include one or more additives that may provide additional mechanical abrasion within the animal's mouth upon chewing or improve an animal's oral condition through ingestion and compliment or boost the influence of *Ascophyllum nodosum* in treating plaque or calculus.

For example, the base composition may also include abrasive additives, breath sweeteners or compounds that may be ingested for improving oral health. Abrasive additives may include calcium carbonate, talc, sodium bicarbonate, etc. The abrasive additive may exhibit a Mohs hardness of 4 or less, including all values and ranges therein such as 0.5 to 4. In addition, the abrasive additive may be present between about 5-10% by weight of the resin composition. Breath sweetening agents may also be incorporated into the base compositions herein. Such agents may include mint, spearmint, peppermint or wintergreen and may also include parsley, chlorophyll, etc. Other ingestible compounds for improving oral health may include, but are not limited to, alma, bilberry fruit, hawthorn berry, Echinacea, goldenseal, folic acid, olive leaf extract, aloe vera, cranberry, licorice root, spirulina, horsetail, coenzyme Q10, yellow dock root, alfalfa leaf, cinnamon bark and tumeric root. The compounds may also include Vitamin C alone or in combination with sodium hexametaphosphate. Breath sweetening and ingestible compounds may individually be present in the range of 0.01 to 5.0% by weight of the base composition, including all values and ranges therein at 0.01% increments. In addition, the total amount of breath sweetening or ingestible compounds may be present in the range of 0.01 to 25.0% by weight of the base composition.

Various additional additives may be added to the resins and rawhide contemplated herein. Such additives may include fiber, plasticizers, colorants, flavorants, olfactory stimulants, etc. In addition, nutrient sources, such as sources of micronutrients, macronutrients and other dietary supplements may be incorporated. For example, with regard to starch based animal chews, various additional additives may include those discussed further herein.

In some embodiments, the starch composition may include cellulose. The cellulose may be, for example, a long-chain polymer of polysaccharide carbohydrate. The cellulose may also be derived or extracted from plants. The cellulose may be incorporated into the starch composition between about 1-15% by weight of the starch composition (understood herein to be the total weight of the starch composition) and any increment or value therebetween including 4%, 10%, 11%, etc.

Emulsifiers or surfactants may also be incorporated into the starch composition. The emulsifier may be present between about 1-10% by weight of the starch composition and all increments or values therebetween including 3%, 4%, etc. The emulsifier may include, for example, lecithin, which may be extracted or derived from, for example, egg yolk or soy beans.

The starch composition may also include a plasticizer. The plasticizer may include for example, glycerin. The plasticizer may be incorporated between about 15-30%, including all increments and values therebetween such as levels greater than 15%, 21%, 27% etc.

A humectant may also be incorporated into the starch composition. The humectant may include, for example, oat fiber. The humectant may be incorporated between about 0.1-5% by weight of the starch composition including all intervals and values therebetween, including 1%, 25%, etc. A humectant may be understood to be any additive that may absorb water in the material.

The starch composition may also include water. The water may be introduced into the composition between about 1-40% by weight of the starch composition and any increment or value therebetween, including 4%, 20-40%, 10-20%, etc. After the product has been formed, the water may be present between 1-20% by weight of the starch composition including all increments or values therebetween, such as, below 20%, 4%, 5-10%, etc.

The starch composition may include a nutraceutical. The nutraceutical may be fermented soya. Fermented soya nutraceuticals are available from Bio Food, Ltd., Pine Brook, N.J. and sold under the general trademark Soynatto®. The fermented soya is present between about 1-40% by weight of the starch composition, including all increments and values therbetween, including 10%, 20%, etc.

The starch composition may also include saccharomyces cerevisiae, commonly known as "bakers yeast" or "brewers yeast." *Saccharomyces cerevisiae* is more traditionally known to ferment sugars present in flour or dough, yielding carbon dioxide and alcohol. The *saccharomyces cervisiae* may be present in the starch composition in the range of 0.1 to 5% by weight.

The starch composition may also include enzymes and/or co-enzymes which are similarly available through Bio Foods, Ltd., Pine Brook, N.J. and sold under the trademark of BT-CoQ10®. This reportedly is a biologically transformed (fermented) cell mitochondrial coenzyme and contains Coenzyme Q10 (discussed further herein), antioxidants, phytonetrients and cofactor mineral nutrients and other cell constituents. The enzymes and/or co-enzymes may be present between 0.1-10% by weight of the starch composition, including all increments and values therebetween such as 1%, 5%, etc.

Many of the additives discussed above may also be incorporated into synthetic resins or rawhide, such as cellulose, plasticizers, humectants, nutraceuticals, etc. Other additives may also be introduced into the base compositions (edible or synthetic alike) as well. These additives may include vegetable matter, fruit matter, rawhide, nuts, nut bits or nut flour such as peanut flour, and animal or fish products, by-products, meal or digests, etc. Glutens may also be incorporated into the base compositions. Gluten may be understood as water-insoluble protein complex extracted from cereal grains such as maize or corn and wheat. These additives may be present individually or cumulatively between about 0.1-50% by weight of the starch composition and all increments and values therebetween including 0.1-5.0%, 15%, 25%, etc.

Additionally, as alluded to above, herbs, herbal extracts, vitamins, minerals, and attractants, may be incorporated into the base compositions. For example, in the case of dogs, preferred minerals may include calcium, phosphorus, potassium, sodium, chloride, magnesium, iron, copper, manganese, zinc, iodine, selenium. However, it is to be noted that other trace minerals have been suggested, such as Co, Mo, Cd, As, Si, V, Ni, Pb and Sn. Furthermore, minerals such as potassium, calcium, phosphorous and magnesium may be required in gram amounts/day, whereas iron, zinc, copper, iodine, and selenium are only required in mg or μg/day. The chew herein can therefore be modified to reflect a higher or lower concentration of a given mineral, according to nutritional requirements.

Turning next to the herbal component, the herbs may be selected from the group consisting of St. Johns Wort, Kava Kava, Ginkgo Biloba, Ginseng (Asian or Siberian varieties), and mixtures thereof. Other herbs include Catsclaw, Camomile, Saw Palmetto, Valerina, V. Agnus-Castus, Black Cohosh, and Milk Thistle. Herbs may also include aloe, astragalus, burdock, chestnut, coriolus, versicolor, couchgrass, crampbark, dandelion root, dong quai, elecampane, evening primrose, eyebright, false unicorn root, feverfew, garlic ginger, gota kola, grape seed extract, green tea, guggulipid, hops, ivy, milk thistle, mistletoe (American Asian and European varieties), motherwort, oats, osha, passion flower, pumpkin pygeum, red clover, rosemary, sarsaparilla, skullcap, saw palmetto, stinging nettle, wild indigo, wild yam and yerba mansa. In addition, glucosamines and/or chondroitin can be added to any of the embodiments described herein.

Attractants may include compounds listed herein in addition to animal or fish digests, or other compounds that may increase an animal's interest in the resin composition.

The above additives (minerals, herbs and attractants) may be present individually or cumulatively between about 0.01-25% by weight of the starch composition and any increment or value therebetween including 0.01-0.5%, 10%, 20%, etc.

In another aspect, the present disclosure relates to a method of forming animal chews including *Ascophyllum nodosum*. As alluded to above, the *Ascophyllum nodosum* may be introduced either before, after or while forming the base composition of the chew. Embodiments herein describe the incorporation of the *Ascophyllum nodosum* into a starch composition. However, a person of ordinary skill in the art may adapt the processes herein for use in a synthetic resin composition as well.

Figure 2:
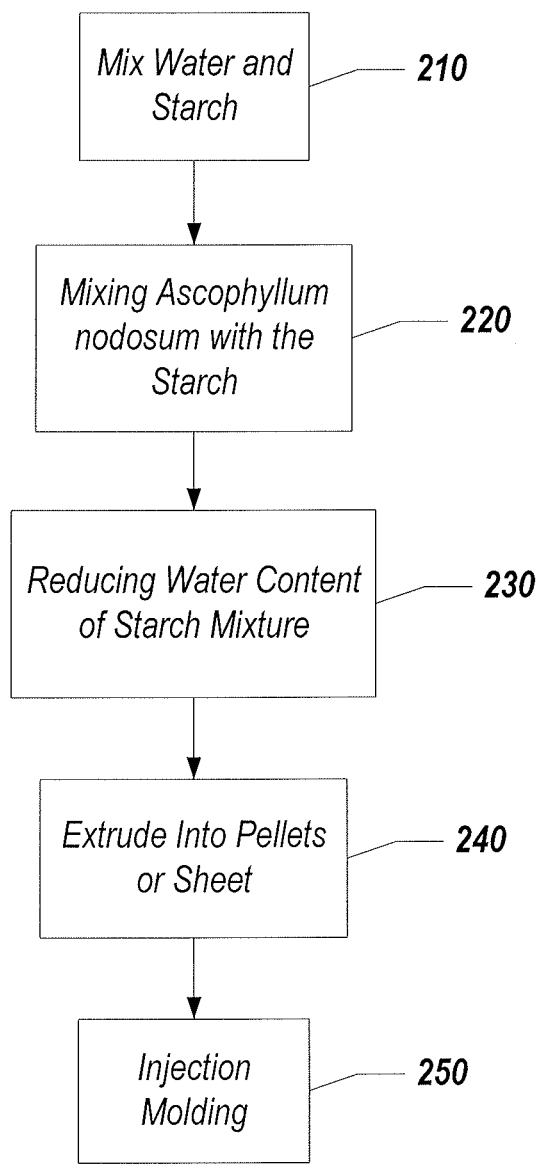
FIG. 2 illustrates an embodiment of a method of forming an animal chew incorporating *Ascophyllum nodosum;*

For example, in one embodiment of forming an animal chew, the *Ascophyllum nodosum* may be incorporated into the starch prior to molding as illustrated in the flow chart of FIG. 2. The process may begin with adjusting the water content of the starch by adding water to the starch, which may be present in the range of 20% to 40% by weight with respect to that of the starch, including all values and ranges therein, and mixing of the water with the starch material 210. The *Ascophyllum nodosum* may also be added to the starch and mixed therein 220. The mixing of the starch, water and/or *Ascophyllum nodosum* may be preformed in a preconditioner or in a plasticating device, as discussed further below.

This may then be followed by a reduction of the water content of the starch mixture 230. This reduction may be facilitated by placement of the starch mixture into a plasticating device, such as an extruder, twin screw extruder, injection molding machine, etc. Plastication may be understood as the input of heat, mechanical action or both, into a material, which may result in a change in the material's viscosity. In this embodiment, a twin screw or single screw extruder may be utilized. In the context of the present invention, where the water level charged in the extruder is preferably lowered during the course of extrusion, an extruder that is configured for venting may be employed, wherein such venting lowers the water level to a desired level. To facilitate such water level change, it may be particularly useful to apply a light vacuum to the extruder barrel at the vent port, to thereby provide a more efficient removal of water from the extrudate therein.

The resulting products of extrusion may be conveniently formed 240 in various shapes. For example, the resulting products may be formed into the shape of beads, the size of which can be made to vary in accordance with standard pelletizing equipment. Or, the resulting products of extrusion may be formed into sheets, which may then be formed into rolls, cut or punched into a desired shape.

Once extruded bead is produced, the water level of the bead exiting the extruder is less than the water level of the starch/water mixture entering the extruder. In the context of the present invention, it has been appreciated that by starting at the starch/water levels herein, one may effectively insure that one will ultimately proceed to injection molding, if so desired at an adequate water level to provide for a stable melt (non-degrading) and injection mold a quality starch product with improved performance characteristics.

Subsequent to recovery of the starch/water extrudate, optionally, the extrudate may be placed into a dryer at various periods of time, from 1 hour to 96 hours, including all values and ranges therein, wherein the water level of the extrudate is lowered an additional amount depending upon dryer conditions. Preferably, the water level of the starch/water extrudate may be lowered within the range of about 15% to 20% by weight of the weight of the product, at which point the extrudate is in condition for injection molding. Further drying may occur, or drying at higher temperatures to produce a final product having a moisture level in the range of 5% to 20% by weight of the weight product, including all values and ranges therein.

In some embodiments, the extruded products (the beads or pellets) may then be injection molded 250. In the step of injection molding, preferably, the injection molding technique is similarly configured to reduce moisture content once again, to a final level that is at or below about 20% by weight of the starch material. However, in preferred embodiment, the final level of water in the molded product is between about 5% to 20% by weight of the molded product, in a more preferable embodiment the water level of the molded product is set to about 10-15% by weight, and in a most preferred embodiment, the water level of the molded product is set to about 11-14%, or 11-13% by weight. It has been found, therefore, that by sequencing the loss of water, from extrusion, to injection molding, one may achieve outstanding quality for the various shaped products produced in accordance with such step-down in moisture levels through-out the melt processing history disclosed herein.

In that regard, the initial zone or zones of the injection molding machine may be cooled proximate the hopper feed section to improve the quality of the injection molded parts produced herein. Those skilled in the art will appreciate that an injection molding machine may typically contain a hopper feed section, a barrel and an output nozzle, including a plurality of heating zones in the barrel extending from the hopper section to the nozzle. The temperature in the first zone adjacent the hopper may be heated at a temperature of less than about 150° F. More preferably, the first zone adjacent the hopper may be set in the range of about 45-150° F. In an even more preferred embodiment, i.e., that situation wherein there is a first zone adjacent the hopper, and a second zone adjacent the first zone, the temperatures of the first zone may be set to about 45-70° F., and the second zone may be set to about 70-150° F. These temperatures may be achieved by the use of cooling cools placed about the barrel of the injection molding machine, said cooling cools comprising copper cooling cools with circulating water.

In a particularly preferred embodiment, the following temperature profile may be applied to a standard injection molding machine: Zone 4 (closest to hopper)=45-70° F.; Zone 3=70-150° F.; Zone 2=150-300° F.; Zone 1=275-375° F., Nozzle=275-390° F. In addition, bushing (inside the mold) is preferably set at about 325-425° F. The mold temperature may be set at 35-65° F.

Any additional additives may be added during the preconditioning process, extrusion process or the injection molding process. In some embodiments, depending on the sensitivity or mixability of the additives, different additives may be added at different steps during the process or may be added multiple times during a process.

Figure 3:
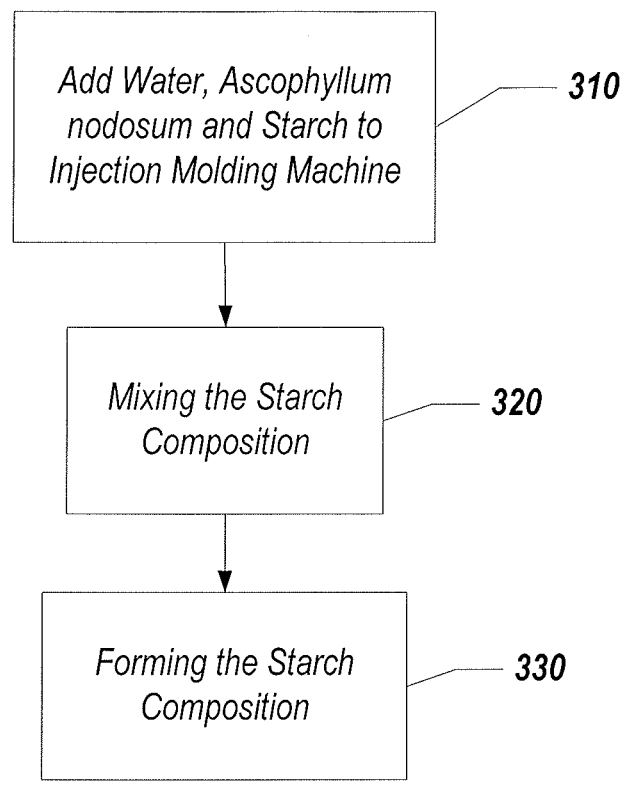
FIG. 3 illustrates a further embodiment of a method of forming an animal chew incorporating *Ascophyllum nodosum;*

In other embodiments, the *Ascophyllum nodosum*, starch, water and any additional additives may be directly injection molded. The term "direct" as used herein with respect to injection molding refers to the molding of starch without exposing the starch to prior thermal molding histories before injection molding. However, the starch herein may, e.g., be heated for drying purposes, which would not amount to a prior thermal molding history. Accordingly, in such an embodiment, as illustrated in FIG. 3, the additives of the starch composition may be introduced directly into the barrel of an injection molding machine through a hopper or other feeding device 310. In addition, water may be added to the starch in the range of 20% by weight to 40% by weight, including all values and ranges therein. Various feeding devices for introducing the additives into the injection molding barrel may be contemplated including loss-in weight gravimetric blenders/feeders, auger feeders, venturi loaders, etc. Those skilled in the art will appreciate that an injection molding machine may typically include a barrel including a feed section, a screw and an output nozzle. The barrel may include a plurality of temperature control zones in the barrel extending from the feed section to the nozzle. The injection molding machine may include a mold having one or more cavities. The molding machine may also be vented, including a vented barrel and/or a vented mold.

The temperature adjustment may vary for each zone. For example, in one exemplary embodiment, the molding machine barrel may include 4 zones, zone 1 being the closest to the feed section and zone 4 being the closest to the nozzle. Zone 1 may be set to less than about 150° F., including any increment or value between about 35 to 150° F. including between about 46 to 150° F., 46 to 70° F., etc. Similarly zone 2 may be set between about 70 to 150° F. including any increment or value therebetween, zone 3 between about 50 to 300° F. including any increment or value therebetween, and zone 4 between about 200 to 375° F. including any increment or value therebetween. The nozzle may be set between about 250 to 390° F. including any increment or value therebetween. The bushing inside of the mold may be set between about 250 to 425° F. including any increment or value therebetween and the mold may also be set between about 35 to 65° F. including any increment or value therebetween.

Once introduced into the barrel of the molding machine the additives may be blended with the starch 320 as the screw conveys the material towards the mold where the starch composition may be formed 330. The mold may cool the starch composition. Once molded, and venting takes place, the starch composition may include water between about 1-20% by weight of the product composition, including all increments and values therebetween such as 10%, 15%, etc. The starch composition may be molded into any form capable of being produced in an injection molding cavity.

Figure 4:
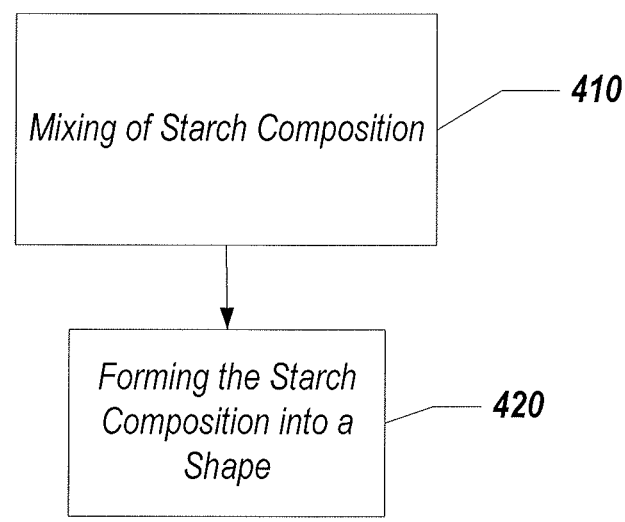
FIG. 4 illustrates yet a further embodiment of a method of forming an animal chew incorporating *Ascophyllum nodosum;*

In yet another embodiment, illustrated in FIG. 4, the starch composition may be formulated and plasticated (either in an extruder or an injection molding machine) 410 without adding *Ascophyllum nodosum* to the base composition. The base composition may then be formed into a desired shape 420.

After formation of the base composition (either with or without adding *Ascophyllum nodosum* to the base composition), the starch composition may be relatively sticky and exhibit a moisture content in the range of 5% by weight of the product to 20% by weight of the product, including all values and ranges therein. In addition, the starch composition may exhibit a temperature that is 10° F. to 80° F. above ambient temperature or 70° F., including all values and ranges therein. The *Ascophyllum nodosum* may be applied to the relatively tacky surfaces of the animal chew, adhering to the animal chew. As the animal chew continues to cool and/or the moisture content is reduced, the *Ascophyllum nodosum* may remain on the surface of the animal chew.

In further embodiments, an adhesive composition may be applied to the surface of the animal chew prior to applying the *Ascophyllum nodosum*. The adhesive composition may include, for example, pasteurized egg whites, albumin, an aqueous solution of tylose powder, or other edible adhesives. The adhesive composition may be applied to the surfaces upon which the *Ascophyllum nodosum* will be applied. After applying the adhesive, the *Ascophyllum nodosum* may be applied to the surface of the base composition and the edible adhesive may be dried.

Figure 5A:
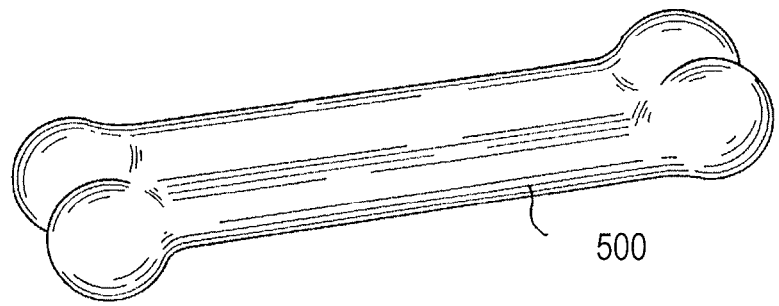
FIGS. 5a through 5c illustrates an additional embodiment of an animal chew that may incorporate *Ascophyllum nodosum.
Figure 5B:
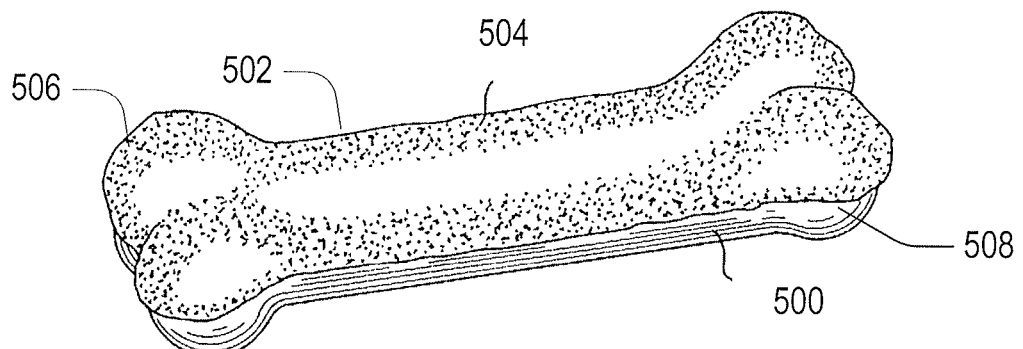
Figure 5C:
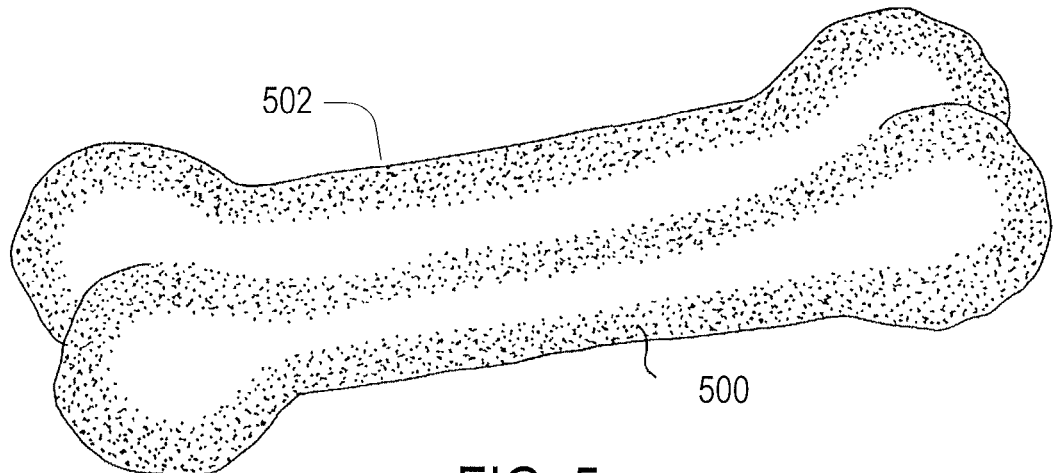

FIG. 5a illustrates an example of an animal chew 500 after forming the chew into a desired shape, which may be produced by injection molding. As illustrated in FIG. 5b, the *Ascophyllum nodosum* 502 may be applied to selected surfaces of the animal chew 500 prior to complete cooling of the animal chew to ambient temperature. While it is illustrated in FIG. 5b that the *Ascophyllum nodosum* 502 is applied to a longitudinal surface 504 of the animal chew, the *Ascophyllum nodosum* may also be applied only upon one or more ends of the animal chew 506, 508 or other selected surfaces. FIG. 5c illustrates another embodiment wherein the *Ascophyllum nodosum* 502 is applied to the entire exterior surface of the animal chew 500.

Figure 6:
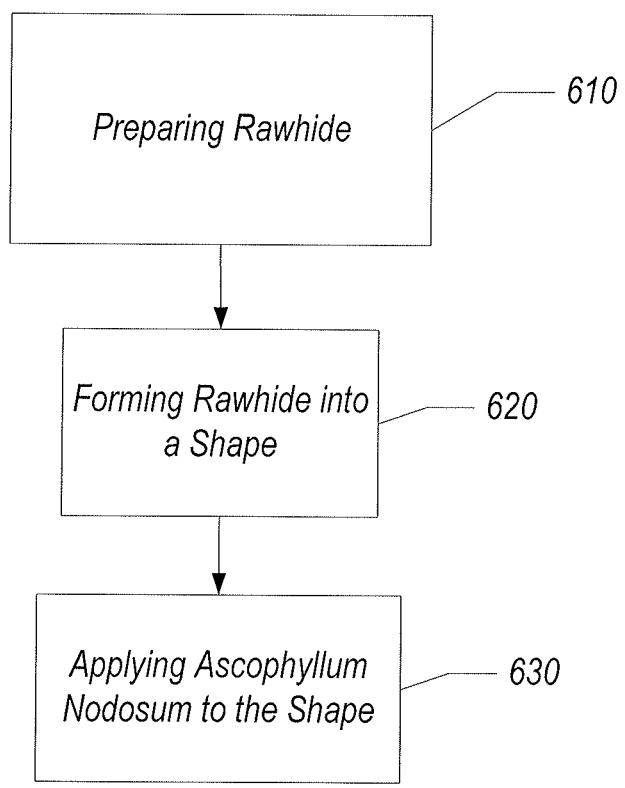
* and FIG. 6 illustrates another embodiment of a method of forming an animal chew incorporating *Ascophyllum nodosum*

In yet additional embodiments, an example of which is illustrated in FIG. 6, sheets of rawhide may be prepared 610. The rawhide may be obtained from the hide of an animal such a buffalo, sheep, goats, marsupials, pigs, deer, elk or cattle. The high may not be exposed to tanning and may be devoid of all fur, meat and fat. The hide may contain between 60 wt % to 80 wt % by water, including all values and ranges therein, and 20% to 40% by weight other substances, including all values and ranges therein. such as fibrous proteins, collagen, keratin, elastin and reticulin. Also, ash may be present between 0.01 wt % to 2.0 wt % by weight of the rawhide, including all values and ranges therein, wherein the ash may include phosphorous, potassium, sodium, arsenic, magnesium and calcium.

Generally, a hide may be prepared by any method known to those of ordinary skill in the art. One such exemplary method may include removing most of the visible fat 4 and meat from the hide. Once the fat and meat is removed the hide may be treated in a solution of calcium carbonate or calcium hydroxide, which may loosen and aid in the removal of hair. In addition, sodium sulphide, ammonium salts or enzymes may be added to the solution. The hair may then be removed from the hide and the hide may be rinsed. The hide may then be soaked in an aqueous solution including organic acids, inorganic acids and/or acid salts, such as potassium hydrogen tartrate and sodium bicarbonate. The hide may be rinsed again forming rawhide pieces, which may assume the shape of sheets. The pieces of rawhide may be dried or further processed wet. In addition, the pieces may be soaked in a solution including hydrogen peroxide and chlorine.

In an exemplary embodiment, the rawhide may be provided as a rawhide resin composition, wherein the rawhide may be chopped or ground into small particles or powder. The particle size may be less than about 10 mm, such as in the range of 0.001 to 10 mm, including all values and increments therein. The rawhide moisture content may be adjusted to approximately 1-20% by weight of the rawhide, including all increments and values therein, such at 8%, 10%, etc. The rawhide may then be combined with up to 20% by weight of casein, such as in the range of about 0.1 to 20% by weight, including all values and increments therein.

Caesin may be understood as a phosphoprotein of milk, wherein a phosphoprotein may be described as a group of substances that are chemically bonded to a substance containing phosphoric acid. The rawhide may also be combined with gelatin up to 10% by weight, such as in the range of 0.1 to 10% by weight, including all values and increments therein. Gelatin may be understood as a protein product produced by partial hydrolysis of collagen. In addition, attractants, such as flavorants, or nutrients may be compounded with the rawhide.

The rawhide particles may be melt processed, wherein the particles are plasticated in a plasticating device. Again, suitable plasticating devices may include injection molding machines, extruders (twin-screw, single screw, etc.) or any other device which may provide sufficient thermal-mechanical interaction to cause plastication, such as blenders. The temperature of the plasticating device may be sufficient to melt at least 10% to 100% of the particles, including all values and increments therein and may be in the range of 5 about 120 to 150 ° C., including all values and increments therein. In addition, the particles may be pressurized during plastication wherein the applied pressure may be in the range of about 1 to 20 MPa, including all values and increments therein. For example, back pressure may be applied during injection molding.

Once plasticated, the rawhide base composition may be formed to a desired shape 620, such as a sheet, strips or a formed article, by an extruder die, an injection mold cavity, etc. The rawhide may also be pelletized for further processing. It should be appreciated that the casein, gelatin and other additives, i.e. attractants, flavoring or nutrients may be added to the rawhide prior to or during plastication. In addition, moisture may be removed from the rawhide during plastication or after plastication. For example, the plastication device may be vented, such as by the use of vent ports in the plastication device. After plastication, the moisture may be removed by drying, such as drying in an oven or tunnel.

The *Ascophyllum nodosum* may be applied to the surface of the rawhide after shaping the rawhide 630. For example, the *Ascophyllum nodosum* may be applied to the rawhide after plasticizing the rawhide and, optionally, a portion of the *Ascophyllum nodosum* may be incorporated into the rawhide during plastication. In other embodiments, an edible resin may be prepared with *Ascophyllum nodosum* which may be incorporated into the rawhide. Once the rawhide is shaped at least a portion of the surface of the rawhide may be coated with at least 10% by weight of the total amount of the *Ascophyllum nodosum* present in the chew.

In may now be appreciated that the present disclosure relates to an animal chew incorporating the *Ascophyllum nodosum* to treat dental plaque and/or calculus though mechanical abrasion and/or biological activity. As used herein, treating may be understood as reducing the amount of dental plaque and/or calculus. The animal, such as a dog, cat or other mammal, may chew or gnaw on the animal chew as formed herein. The interaction of the animal's teeth and gums against the animal chew may result in mechanical abrasion sufficient to remove dental plaque and/or calculus from the animal's teeth. Furthermore, the ingestion of the *Ascophyllum nodosum* and other additives for improving an animal's oral condition may synergistically act to biologicially reduce the dental plaque or calculus from the animal's teeth.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A method of forming an animal chew comprising:
    plasticating a base composition and *Ascophyllum nodosum*;
    forming said base composition into a shape having a surface;
    applying an adhesive composition to said surface, wherein said adhesive is selected from the group consisting of pasteurized egg whites, albumin and an aqueous solution of tylose powder; and
    applying at least 10% of the total amount of said *Ascophyllum nodosum* to the surface of the base composition after processing, wherein said *Ascophyllum nodosum* is added in a total amount of 0.1% by weight to 5.0% by weight of the animal chew and said animal chew exhibits a Shore D hardness, as measured by ASTM D 2240-05 (2010), of 25 to 40 Shore D, and an elongation at break, as measured by ASTM D 638-10 in the range of 1% to 7%.

2. The method of claim 1, wherein said base composition is starch, further comprising:
    mixing water with said base composition, wherein said water is present in the range of 20% to 40% by weight of the base composition; and
    reducing said water content, wherein after forming said base composition said water is present in the range of 1% to 20% by weight of the base composition.

3. The method of claim 1, wherein said base composition is first plasticated in an extruder, formed into beads; and formed into said shape by injection molding.

4. The method of claim 1, wherein said base composition is plasticated, formed and heated in an injection molding machine.

5. The method of claim 1, further comprising adding to said base composition an additive that provides mechanical abrasion, wherein said additive exhibits a Mohs hardness of 4 or less and is present in the range of 5% to 10% by weight of the base composition.

6. The method of claim 1, further comprising adding to said base composition one or more ingestible additive for improving oral health selected from a group of the following:
 alma, bilberry fruit, hawthorn berry, Echinacea, goldenseal, folic acid, olive leaf extract, aloe vera, cranberry, licorice root, spirulina, horsetail, coenzyme Q10, yellow dock root, alfalfa leaf, cinnamon bark, tumeric root, Vitamin C, sodium hexametaphosphate and combinations thereof, wherein said one or more ingestible additives is present in the range of 0.01% to 25.0% by weight of the base composition.

* * * * *